United States Patent [19]
Dubrulle

[11] Patent Number: 5,430,296
[45] Date of Patent: Jul. 4, 1995

[54] APPARATUS FOR TESTING THE QUALITY OF A SHEATH OF THE POLYETHYLENE TYPE

[75] Inventor: Marc Dubrulle, Pont de Briques, France

[73] Assignee: Alcatel Cable, Chichy Cedex, France

[21] Appl. No.: 123,471

[22] Filed: Sep. 20, 1993

[30] Foreign Application Priority Data

Sep. 21, 1992 [FR] France .................. 92 11207

[51] Int. Cl.⁶ .............. G01N 21/01; G01N 21/88; G01N 21/89
[52] U.S. Cl. .............. 250/341.1; 250/358.1; 250/359.1
[58] Field of Search .............. 250/341, 358.1, 359.1, 250/572, 341.1

[56] References Cited

U.S. PATENT DOCUMENTS

| | | | |
|---|---|---|---|
| 2,922,887 | 1/1960 | Jacobs | 250/359.1 |
| 3,629,584 | 12/1971 | Blomgren, Jr. | 250/341 X |
| 4,208,126 | 6/1980 | Cheo et al. | 250/341 X |
| 4,363,966 | 12/1982 | Cheo | 250/341 X |
| 4,550,255 | 10/1985 | Sve et al. | 250/359.1 |
| 4,988,875 | 1/1991 | Ortiz et al. | 250/358.1 X |

FOREIGN PATENT DOCUMENTS

0374796A3 6/1990 European Pat. Off. .
1143243 2/1969 United Kingdom .

OTHER PUBLICATIONS

Oriel Catalog, 'Optics and Filters', vol. III, pp. 4–7.
Cheo, P. K. "Far-infrared Laser System for Detection of Defects in Polyethylene-Insulated Power Cables", Optical Society of America, vol. 2, No. 2, Feb. 1978 pp. 42–44.

Primary Examiner—Constantine Hannaher
Assistant Examiner—Edward J. Glick
Attorney, Agent, or Firm—Sughrue, Mion, Zinn, Macpeak & Seas

[57] ABSTRACT

An apparatus for testing the quality of a sheath of the polyethylene type on a test piece based on the transparency of polyethylene to infrared radiation. The apparatus includes a glass tank (5) containing a bath (4) of refractive index that is close to the refractive index of polyethylene, a test piece (1) received in the tank, a lighting assembly (11) for illuminating the test piece by a light beam (12) of limited aperture angle (a) passing through a light-diffusing screen (10) having narrow diffusion lobes, and an infrared detection assembly (15, 16) for detecting the beam passing through the test piece. The apparatus may be applied for testing the sheaths on splice boxes and on repeater casings.

5 Claims, 1 Drawing Sheet

APPARATUS FOR TESTING THE QUALITY OF A SHEATH OF THE POLYETHYLENE TYPE

BACKGROUND OF THE INVENTION

1. Field of the Invention

The present invention relates to apparatus for testing the quality of a sheath of the polyethylene type, by detecting any defects in the sheath.

2. Description of the Background Art

Such testing is performed on all insulation sheaths. Testing is particularly strict on polyethylene-type sheaths for under-sea links. In particular, such testing must be performed on the overmolded portions of the sheaths and at the interfaces with the overmolded portions, before such a link is laid or after any repairs have been made thereto.

Conventionally, an under-sea link is made up of line cables interconnected directly in splice boxes or via repeaters. Each such repeater is clad with a casing and is provided with two access cables which are themselves connected to the line cables in splice boxes or the like commonly referred to as end boxes. The repeater casings and the splice boxes are individually protected by overmolded polyethylene sheaths co-operating with the sheaths of the cables in question to provide continuity in the sheathing of the link, so that it is waterproof and electrically insulated relative to seawater.

The sheaths of the line cables and of the repeater access cables are made of polyethylene, are extruded and are tested before the cables are used. Such testing is often performed electrically, by passing a current through the cables. When there are defects in the sheath, such testing gives rise to insulation breakdowns in the sheath. Such testing is therefore destructive.

The sheaths overmolded on the repeater casings are tested as soon as the repeaters have been equipped with their access cables, and the sheaths overmolded on the splice boxes are tested as soon as the cables in question have been interconnected.

Until now, such overmolded sheaths and their interfaces with the sheaths of the cables have been tested with X-rays, so as to detect any metallic inclusions in the sheaths or at the interfaces.

Such X-ray testing is particularly dangerous for operators, and requires highly skilled operators. It is costly and time-consuming to perform. It is also insensitive to non-metallic defects, such as for example "voids" or air bubbles, which may, like metallic inclusions, give rise to insulation breakdowns during electrical testing prior to laying the link or prior to bringing it into service.

A method of inspecting polyethylene sheaths on electrical cables is known that is based on the transparency of polyethylene to infrared radiation.

A known apparatus uses a laser emitting coherent near-infrared light to perform non-destructive testing of the quality of a polyethylene-type sheath, by detecting any defects regardless of the nature of the defects.

An object of the present invention is to provide an apparatus that is simple to implement and that makes it possible to obtain optimum resolution of defects in a cable sheath or in a sheath overmolded on an equipment casing or on a cable splice box.

SUMMARY OF THE INVENTION

The invention provides apparatus for testing the quality of a sheath of the polyethylene type covering a member of a different type, and forming therewith a test piece, said apparatus including:

a lighting assembly directing an "incident" light beam containing infrared radiation at said test piece, transversely thereto and at least over the height thereof; and an infrared detection assembly receiving the incident beam after it has passed through said test piece, at which point the beam is referred to as the "analysis" beam;

said lighting assembly and said detection assembly being in optical alignment and being on opposite sides of said test piece;

said apparatus being characterized in that it further includes a light-diffusing screen having narrow diffusion lobes associated with said lighting assembly and that is interposed in the path of said incident beam which is thus formed of diffuse light entering into said test piece.

The invention further has at least one of the following additional characteristics:

said lighting assembly includes a light source, a slot, and optical means, delivering said beam with a limited aperture angle over a given "useful test" length of said test piece via said screen;

said aperture angle is preferably substantially 19°, and said screen is a "Marata" filter; and said test piece is installed in a tank which is transparent to the incident beam and which contains a bath of refractive index that is close to the refractive index of polyethylene, in which bath said test piece is immersed.

BRIEF DESCRIPTION OF THE DRAWINGS

The characteristics and advantages of the present invention appear from the following description of embodiments given by way of example and with reference to the accompanying drawings, in which.

DETAILED DESCRIPTION OF THE PREFERRED EMBODIMENTS

Figure 1:
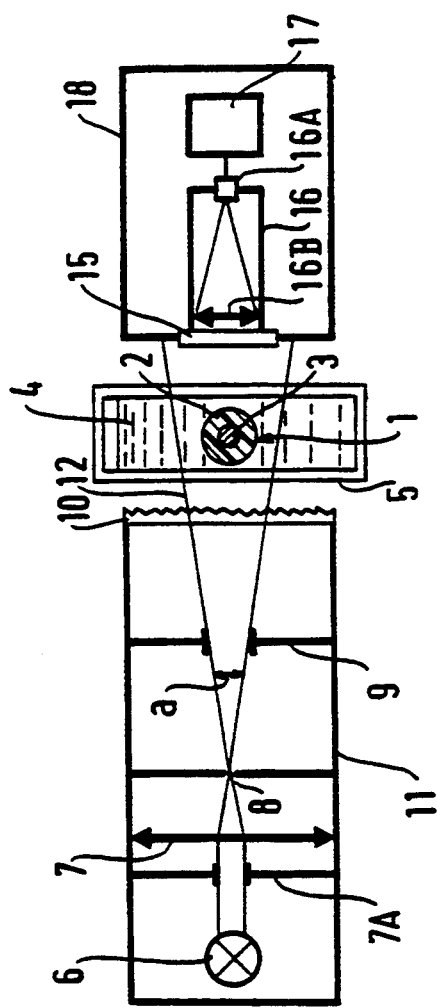
FIG. 1 is a diagram showing a preferred embodiment of the test apparatus of the present invention.
Figure 2:
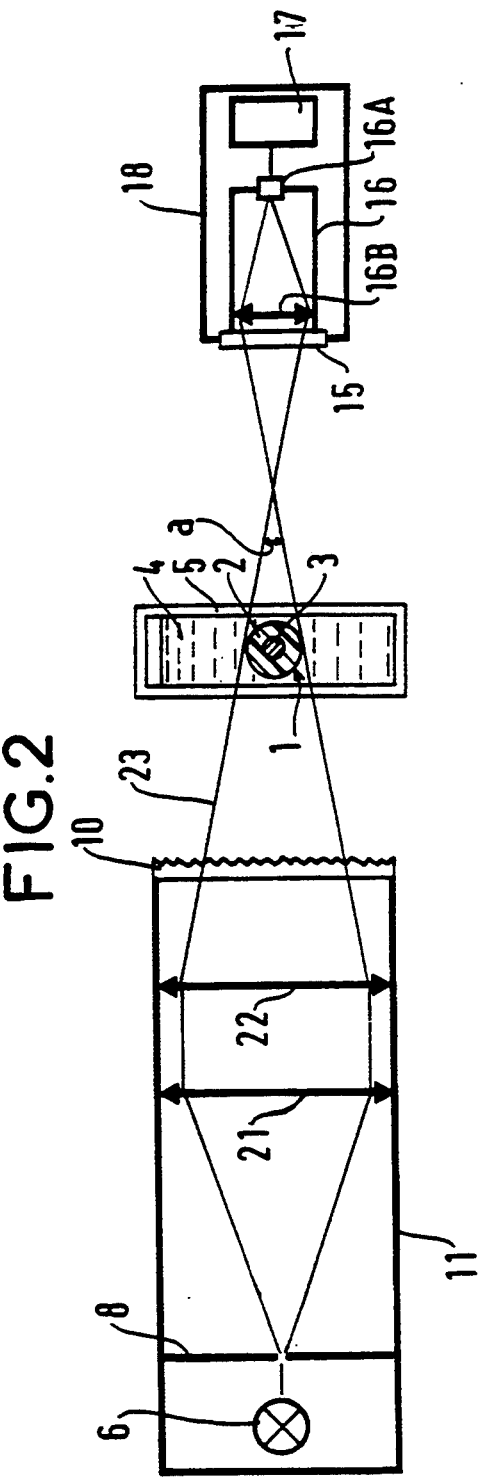
FIG. 2 is a diagram showing a second embodiment of the apparatus shown in FIG. 1.

The apparatuses shown in FIGS. 1 and 2 test the quality of a polyethylene sheath, and of any interfaces with other sheaths, also made of polyethylene. The sheath may be a sheath on a cable or preferably a sheath that is overmolded either on a splice box for splicing together two cables, or else on a repeater casing.

The member sheathed with its polyethylene sheath whose quality is to be tested is referred to below as the "test piece". Testing is based on the transparency of polyethylene to infrared radiation.

In FIGS. 1 and 2, the test piece 1 is shown in section and formed by a sheath 2 to be tested which covers a metal member 3. For the test, the test piece is installed in a bath 4 contained in a glass tank 5. The refractive index of the bath is chosen to be close to the refractive index of polyethylene, and the bath is in particular constituted by VASELINE petroleum jelly. The test piece immersed in the bath is carried by two opposite walls of the tank through which it passes in a sealed manner, and in which it can be rotated about its own axis and can be driven in translation, depending on the type of the test piece in question.

With reference to FIG. 1, in addition to the tank 5 and the bath 4 contained thereby, the apparatus includes a lighting assembly constituted by a broad-spectrum light source 6, a lighting optical system 7 having an associated shutter 7A, a slot 8, a diaphragm 9, and a light-diffusing screen 10 having narrow diffusion lobes. The lighting assembly is installed on one side of the tank and facing the test piece 1. The lighting assembly is disposed in a "lighting" housing 11, on which the screen forms the lighting face. The lighting assembly delivers a light beam 12 of limited aperture angle (referenced a), which beam illuminates the test piece over the entire height thereof and over the "useful test" length thereof.

On the other side of the tank 5, but also facing the test piece, the apparatus includes an infrared filter 15, an infrared detection camera 16, and a printing system 17 coupled to the camera, forming a detection and image printing assembly 18. The filter and the camera preferably operate in the near-infrared range, which corresponds to the best transmission band of polyethylene. Advantageously, the camera is a strip 16A, referred to as a "CCD-type" strip, i.e. having charge-coupled devices, which is coupled to an input lens 16B. The filter is mounted on a plate limiting image detection and observation substantially to the maximum transverse dimension of the test piece, and to the useful test length thereof.

Advantageously, the printing system is a thermal printer.

In the lighting assembly installed in the housing 11, the lighting optical system forms an image of the source 6 over the length of the slot 8, which thereby acts as a narrow linear source and delivers a light beam 12 which is then divergent. The aperture angle of said light beam is centered on the width of the source slot 8 and is limited by the diaphragm 9, thereby making it possible to adapt the incidence of the rays in the beam 12 that enter into the bath and the test piece so as to obtain limited light diffusion therein. By choosing such limited light diffusion in the polyethylene, resolution losses are reduced, and it is possible to show up small defects without giving a structural analysis of the composition of the illuminated bath and of the illuminated polyethylene.

The bath 4 enables the thickness of polyethylene through which the beam 12 passes to be made uniform, by limiting refraction phenomena at the optical surfaces formed by the outside surface of the sheath. The screen 10 having narrow diffusion lobes in turn provides light diffusion that is as close as possible to the limited diffusion in the polyethylene.

Experiments conducted by the Applicant have shown that the limited aperture angle must remain less than about 30°, and should preferably be 19° with a screen having narrow lobes that is of the "Marata" filter or screen type. The resolution achieved under these conditions makes it possible to detect small defects, of about 0.1 mm.

In the variant shown in FIG. 2, elements identical to those in FIG. 1 are given the same references. The changes made relate solely to the lighting system, and only the changes are described below.

The changes consist essentially in the lighting optical system interposed in FIG. 1 between the source 6 and the slot 8 being replaced by a collimating optical system 21 and a focusing optical system 22, which systems are, in this case, interposed between the slot 8 and the light-diffusion screen 10, and process the light beam received from the source via the slot 8. The light beam 23 is still of limited aperture angle, but is convergent in this variant.

The lighting system modified in this way enables the light passing through the polyethylene onto the lens of the camera to be concentrated to a greater extent. However, this system is less compact than the system shown in FIG. 1.

The optical test apparatus of the invention enables the quality of a sheath to be detected accurately, with excellent contrast close to the inside edge of the sheath. The devices is compact and relatively easy to adjust. The apparatus makes it possible to determine the dimensions of the defects and to deduce the nature thereof, such as an air-filled hole, or a metallic inclusion for example. There is no danger for the operator and no special qualification is required of the operators. The sheath can be fully tested by rotating the test piece in the bath and, depending on the test piece, by moving it in translation. In a variant the sheath of a cable may be fully tested without rotating the cable by means of two or more optical apparatuses which are mounted one after another along the cable and which are angularly offset relative to one another.

We claim:

1. Apparatus for testing the quality of a sheath of the polyethylene type covering a member of a different type, and forming therewith a test piece, said apparatus including:

a lighting assembly directing an incident light beam containing infrared radiation at the test piece, transversely thereto and at least over the height thereof; and an infrared detection assembly receiving the incident light beam after it has passed through the test piece, wherein said lighting assembly and said detection assembly are in optical alignment and on opposite sides of said test piece, and wherein said apparatus further comprises a light-diffusing screen interposed in the path of the incident light beam between said lighting assembly and the test piece said light-diffusing screen having narrow diffusion lobes that receive the incident light beam and that diffuse the incident light beam to substantially the same extent as the polyethylene sheath.

2. Apparatus according to claim 1, wherein said lighting assembly comprises a light source, a source-slot, and associated optical means, for delivering the incident beam with limited aperture angle over a predetermined length of the test piece via said screen.

3. Apparatus according to claim 2, wherein said aperture angle is substantially 19°.

4. Apparatus according to claim 1, wherein said screen is a "Marata" filter.

5. Apparatus according to claim 1, further comprising a tank which is transparent to the incident beam and which contains a bath having a refractive index that is close to the refractive index of polyethylene, in which bath the test piece is immersed.

* * * * *